(12) United States Patent
Leohr

(10) Patent No.: US 8,355,877 B2
(45) Date of Patent: *Jan. 15, 2013

(54) SYSTEM FOR PREDICTING RESPONSIVENESS TO A PHARMACEUTICAL THERAPY FOR OBESITY

(75) Inventor: Jennifer K. Leohr, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 90 days.

This patent is subject to a terminal disclaimer.

(21) Appl. No.: 12/743,034

(22) PCT Filed: Dec. 18, 2008

(86) PCT No.: PCT/US2008/087386
§ 371 (c)(1),
(2), (4) Date: May 14, 2010

(87) PCT Pub. No.: WO2009/085927
PCT Pub. Date: Jul. 9, 2009

(65) Prior Publication Data
US 2010/0268474 A1    Oct. 21, 2010

Related U.S. Application Data

(60) Provisional application No. 61/014,881, filed on Dec. 19, 2007.

(51) Int. Cl.
*G01N 33/92* (2006.01)
(52) U.S. Cl. .......................... 702/19; 324/318
(58) Field of Classification Search .................. None
See application file for complete search history.

(56) References Cited

U.S. PATENT DOCUMENTS

| 5,343,389 | A | 8/1994 | Otvos |
| 6,617,167 | B2 | 9/2003 | Otvos et al. |
| 2005/0169839 | A1 | 8/2005 | Fong et al. |
| 2005/0222504 | A1 | 10/2005 | Otvos et al. |

FOREIGN PATENT DOCUMENTS

| WO | 0051054 A1 | 12/1999 |
| WO | 2007039184 A2 | 4/2007 |

OTHER PUBLICATIONS

Karpe, et al, "Differences in Postprandial Concentrations of Very-Low-Density Lipoprotein and Chylomicron Remnants Between Normotriglyceridemic and Hypertriglyceridemic Mem With and Without Coronary Heart Disease"; Metabolism, vol. 48, No. 3 Mar. 1999; pp. 301-307.
Otvos, et al., "NMR Lipoprotein Subclass Analysis: NMR LipoProfile Research Service Description"—Research and Development Division, James Otvos, Ph.D.,Chief Scientific Officer.
Otvos, "Technical Bulletin—Mar. 1, 2004, NMR LipoProfile—II Subclass Particle Analysis", James D. Otvos, LipoScience, Inc.
Otvos, "NMR LipoProfile Data Analysis Guide", 2003.
Otvos, "Measurement of Lipoprotein Subclass Profiles by Nuclear Magnetic Resonance Spectroscopy" supplied by the British Library—"The world's Knowledge", pp. 609-623.
Suter, et al., "Effect of orlistat on postprandial lipemia, NMR lipoprotein subclass profiles and particle size", Atherosclerosis, 180, 2005, pp. 127-135.

*Primary Examiner* — Michael Borin
(74) *Attorney, Agent, or Firm* — R. Craig Tucker

(57) ABSTRACT

Methods, systems, and computer program products using TRL V6 as a biomarker for the modulation of triglyceride and/or lipoprotein metabolism in a mammal induced by an investigational weight loss pharmaceutical agent. The biomarker may be used for predetermining if an individual patient will likely respond favorably to a given weight loss pharmaceutical agent and/or for testing a pharmaceutical agent's ability to modulate triglyceride and/or lipoprotein metabolism in a mammal.

1 Claim, 5 Drawing Sheets

SYSTEM FOR PREDICTING RESPONSIVENESS TO A PHARMACEUTICAL THERAPY FOR OBESITY

This application claims the benefit of priority to U.S. Provisional Application Ser. No. 61/014,881, filed Dec. 19, 2007.

Multiple physiological systems are involved in regulating body weight and energy homeostasis and these systems are interrelated through multiple complex feedback mechanisms. Though this complexity gives rise to a multiplicity of therapeutic targets amenable to drug therapy, the complex inter-regulation also makes development of effective pharmacological treatment of obesity and overweight difficult and time consuming.

In addition, once a generally effective pharmacological agent is found for the treatment of obesity and/or overweight, genetic and/or physiological differences between individuals may give rise to large variances in efficacy within a patient population; that is there is a tendency for subpopulations of patients to be responders or non-responders to a therapeutic agent based on the individual's physiology. As a result, it is difficult to predict prior to a prolonged course of therapy whether or not a given individual will respond well to a given drug therapy.

It would be of great value to have methods to determine if a compound will likely have the desired physiological effect on body weight and/or energy homeostasis prior to prolonged clinical testing for therapeutic weight loss. It would also be of great value to have methods for predetermining whether an individual patient will respond favorably to the therapeutic effects of a particular weight loss pharmaceutical agent preferably prior to the initiation of a course of therapy with that agent. The present invention provides a biomarker and methods, systems and computer program products for using the biomarker for testing a pharmaceutical agent's ability to modulate triglyceride and/or lipoprotein metabolism in a mammal, which is turn is indicative of the agent's likely physiological benefit for the treatment of obesity and/or overweight.

In one aspect of the present invention, it has been found that changes in the concentration of large triglyceride rich lipoprotein particles of the V6 subclass (TRL V6) can be used as a biomarker for the modulation of triglyceride and/or lipoprotein metabolism in a mammal induced by a weight loss pharmaceutical agent. Specifically, a pharmaceutical agent suitable for the treatment of obesity or overweight through modulation of triglyceride and/or lipoprotein metabolism will produce a reduction in TRL V6 concentration in the subject mammal. As such, one embodiment of the present invention provides a method of predicting responsiveness to treatment for obesity or overweight in a human with a weight loss pharmaceutical agent comprising determining in the human whether there is a reduction in TRL V6 response to a fat load in the presence of the pharmaceutical agent compared to the TRL V6 response in the absence of the pharmaceutical agent. Further embodiments include where the pharmaceutical agent is any one compound or any combination of two or more compounds independently selected from the group consisting of a 5-HT$_{2C}$ receptor agonist, a cannabinoid-1 receptor (CB-1) antagonist, a phospholipid diesterase-10 (PDE-10) inhibitor, an orexin-1 antagonist, a serotonin-noradrenaline-dopamine triple reuptake inhibitor (SNDRI), a lipase inhibitor, and/or a lipid absorption receptor inhibitor.

In another aspect of the present invention, there is provided a method for determining if an individual patient will likely respond favorably to a given weight loss pharmaceutical agent, that is, a method for predicting whether an individual patient in need of treatment for obesity and/or overweight will be a responder or non-responder to treatment with a given weight loss pharmaceutical agent, by determining if the agent produces a reduction in the patient's TRL V6 response. In various embodiments of this aspect of the present invention, the weight loss pharmaceutical agent is any one compound or any combination of two or more compounds independently selected from the group consisting of a 5-HT$_{2C}$ receptor agonist, a cannabinoid-1 receptor (CB-1) antagonist, a phospholipid diesterase-10 (PDE-10) inhibitor, an orexin-1 antagonist, a serotonin-noradrenaline-dopamine triple reuptake inhibitor (SNDRI), a lipase inhibitor, and/or a lipid absorption receptor inhibitor.

In another embodiment of this aspect of the invention, there is provided a method for determining the suitability of a weight loss pharmaceutical agent for treating a patient in need of treatment for obesity and/or overweight comprising administering to the patient a dose of the weight loss pharmaceutical agent in conjunction with administering a fat load to the patient, and then determining whether there is a reduction in TRL V6 response to the fat load compared to the patient's TRL V6 response to the fat load in the absence of the pharmaceutical agent, wherein a significant reduction in TRL V6 response indicates the weight loss pharmaceutical agent is suitable for treating the patient and the lack of a significant reduction in TRL V6 response indicates the weight loss pharmaceutical agent is not suitable for treating the patient.

In another embodiment of this aspect of the invention, there is provided a method for determining the suitability of a weight loss pharmaceutical agent for treating a patient in need of treatment for obesity and/or overweight, comprising the steps of:
1) administering to the patient a first fat load;
2) measuring the patient's TRL V6 response to the first fat load;
3) administering to the patient a dose of the weight loss pharmaceutical agent in conjunction with administering to the patient a second fat load;
4) measuring the patient's TRL V6 response to the second fat load;
5) determining whether there is a reduction in TRL V6 response to the second fat load compared to the TRL V6 response to the first fat load;
6) determining the suitability of the weight loss pharmaceutical agent based on the comparative reduction in the TRL V6 response;

wherein a significant reduction in TRL V6 response indicates the weight loss pharmaceutical agent is suitable for treating the patient and the lack of a significant reduction in TRL V6 response indicates the weight loss pharmaceutical agent is not suitable for treating the patient.

In yet another embodiment of this aspect of the invention, there is provided a method for determining the suitability of a weight loss pharmaceutical agent for treating a patient in need of treatment for obesity and/or overweight, comprising the steps of:
1) administering to the patient a dose of the weight loss pharmaceutical agent in conjunction with administering to the patient a fat load;
2) measuring the patient's TRL V6 response to the fat load;
3) comparing the patient's TRL V6 response to the fat load to a standard TRL V6 response to the fat load in the absence of the weight loss pharmaceutical agent;
4) determining the suitability of the weight loss pharmaceutical agent based on the comparing step;

wherein a significant reduction in the patient's TRL V6 response compared to the standard TRL V6 response indicates the weight loss pharmaceutical agent is suitable for treating the patient and the lack of a significant reduction in the patient's TRL V6 response compared to the standard TRL V6 response indicates the weight loss pharmaceutical agent is not suitable for treating the patient.

In another embodiment, there is provided a method for predicting whether a patient in need of treatment for obesity and/or overweight will be a responder to treatment with a given weight loss pharmaceutical agent, comprising the steps of:
1) administering to the patient a first fat load;
2) measuring the patient's TRL V6 response to the first fat load;
3) administering to the patient a dose of the pharmaceutical agent in conjunction with administering to the patient a second fat load;
4) measuring the patient's TRL V6 response to the second fat load;
5) determining whether there is a reduction in the patient's TRL V6 response to the second fat load compared to the patient's TRL V6 response to the first fat load; and
6) predicting whether the patient will be a responder based on the determining step,
wherein a significant reduction in TRL V6 response predicts the patient will likely be a responder.

In another embodiment, there is provided a method for predicting whether a patient in need of treatment for obesity and/or overweight will be a responder to treatment with a given weight loss pharmaceutical agent, comprising the steps of:
1) administering to the patient a dose of the weight loss pharmaceutical agent in conjunction with administering to the patient a fat load;
2) measuring the patient's TRL V6 response to the fat load;
3) comparing the patient's V6 response to the fat load to a standard V6 response to the fat load in the absence of the weight loss pharmaceutical agent; and
4) predicting whether the patient will be a responder to the treatment with the weight loss pharmaceutical agent based on the comparing step;
wherein a significant reduction in the patient's V6 response compared to the standard V6 response predicts the patient will likely be a responder.

In another aspect of the present invention, there is provided a method for determining the ability of a pharmaceutical agent to affect triglyceride and/or lipoprotein metabolism in a mammal comprising measuring the reduction in TRF V6 concentration in the mammal in response to a fat load and/or a high fat diet compared to a placebo related response.

Another aspect of the invention is directed to methods for assessing a patient's likelihood of favorably responding to a weight-loss pharmaceutical agent. The methods include: (a) measuring a level of TRL V6 in at least two in vitro samples from the patient, at least one taken in conjunction with administration of the weight-loss pharmaceutical agent to the patient; (b) electronically identifying whether there is a reduction in TRL V6 level associated with the weight loss agent; and (c) assessing a patient's likelihood of favorably responding to the weight loss pharmaceutical agent based on the identifying step.

Certain embodiments of the invention is directed to computer program products for assessing a patient's likelihood of responding to a weight loss pharmaceutical agent. The computer program product includes a computer readable storage medium having computer readable program code embodied in the medium. The computer-readable program code includes computer readable program code that determines a patient's likelihood of responding favorably to the weight loss pharmaceutical agent based on at least one measurement of TRL V6 taken from an in vitro biosample of the patient.

The computer program code that determines the patient's likelihood of responding favorably may optionally include computer readable program code that compares at least two TRL V6 measurements, at least one taken in conjunction with administration of the weight loss pharmaceutical agent to the patient, and evaluates whether there was a significant reduction in the TRL V6 measurement that was taken in conjunction with the administration of the weight loss pharmaceutical agent.

In some embodiments, the computer program code that determines the patient's likelihood of responding favorably compares two post-prandial samples of the patient, taken at two different times, one in conjunction with the administration of the weight loss pharmaceutical agent.

The at least one measurement of TRL V6 can be an NMR measurement of TRL V6.

Still other embodiments are directed to computer program products for assessing the likelihood of whether an investigational pharmaceutical agent will be effective as a weight-loss treatment in human patients. The computer program product includes a computer readable storage medium having computer readable program code embodied in the medium. The computer-readable program code including computer readable program code that evaluates whether an investigational pharmaceutical agent is likely to be able to be effective as a weight loss treatment in a human patient based on measurements of TRL V6 of in vitro biosamples of laboratory test animals that were administered the pharmaceutical agent or are administered a fat load and/or a high fat diet in conjunction with administration of the investigational pharmaceutical agent.

Yet other embodiments of this aspect of the invention are directed to systems for assessing a patient's likelihood of responding favorable to a weight-loss pharmaceutical agent. The systems include: (a) an NMR spectrometer; (b) at least one processor in communication with the NMR spectrometer. The at least one processor is configured to predict whether a patient is likely to respond favorably to a weight loss pharmaceutical agent based on at least one NMR TRL V6 measurement.

The at least one processor may be configured to compare at least two patient biosamples, the at least two biosamples taken after administration of a fat load, one of the samples also taken in conjunction with administration of the weight loss pharmaceutical agent to the patient. The at least one processor can be configured to compare the biosamples to determine whether there is a significant reduction in TRL V6 for the sample taken in conjunction with the weight loss pharmaceutical agent. A significant reduction in TRL V6 indicates a patient is likely to respond favorably to the weight loss pharmaceutical agent.

Additional embodiments are directed to systems for assessing whether an investigational drug is likely to be effective as a weight loss pharmaceutical agent. The systems include an NMR spectrometer; and at least one processor in communication with the NMR spectrometer. The at least one processor is configured to evaluate NMR signal generated by the NMR spectrometer and determine whether an investigational pharmaceutical agent is likely to be able to be effective as a weight loss treatment in a human patient based on an NMR measured TRL V6 response of in vitro biosamples of laboratory test animals that are administered the pharmaceutical agent or are administered a fat load and/or a high fat diet in conjunction with administration of the investigational pharmaceutical agent.

Still other embodiments are directed to test reports for a patient. The reports include an electronic and/or paper report having a test summary of a patient in vitro biosample that indicates whether the patient had a favorable response to a weight loss pharmaceutical agent based on at least one measure of TRL V6.

In some particular embodiments, the test summary compares at least two NMR measures of TRL V6, the at least two NMR measures of TRL V6 taken from two different post prandial in vitro samples of the patient, one of the postprandial samples also taken in conjunction with administration of the weight loss pharmaceutical agent.

As will be appreciated by those of skill in the art in light of the present disclosure, embodiments of the present invention may include methods, systems, apparatus and/or computer program products or combinations thereof.

The foregoing and other objects and aspects of the present invention are explained in detail in the specification set forth below.

Figure 1:
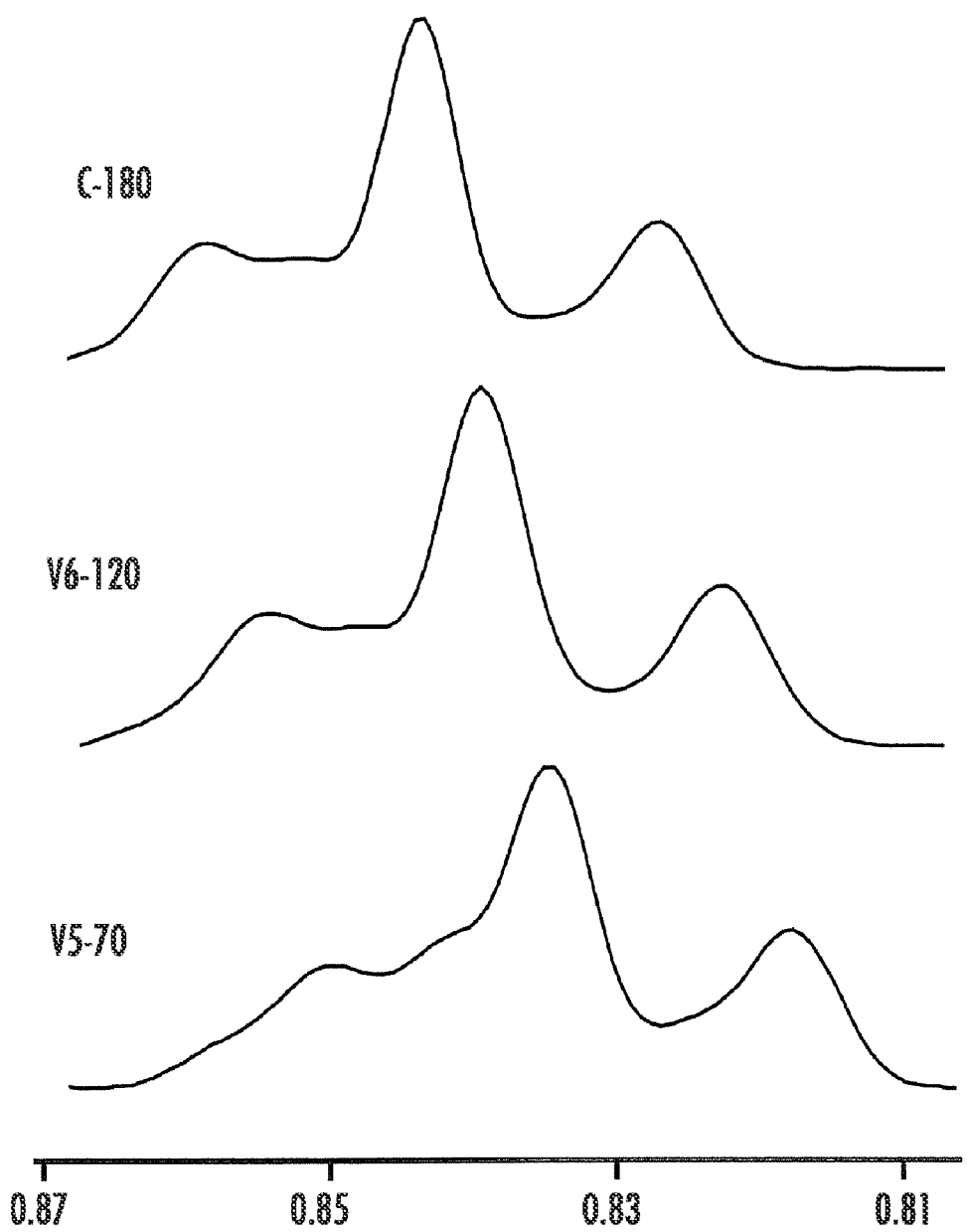
FIG. 1 is a graph of lipid methyl group NMR signals for exemplary triglyceride rich lipoprotein particle subfractions (subclasses).

The present invention will now be described more fully hereinafter, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout, and thickness, size and dimensions of some components, lines, or features may be exaggerated for clarity. The order of operations and/or steps illustrated in the figures or recited in the claims are not intended to be limited to the order presented unless stated otherwise. Broken lines in the figures, where used, indicate that the feature, operation or step so indicated is optional unless specifically stated otherwise.

As will be appreciated by one of skill in the art, some embodiments of the present invention may be embodied as an apparatus, a method, a computer program product and/or data or signal processing system. Accordingly, certain method embodiments do not require software limitations, while certain other embodiments may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, superconducting magnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java7, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this application and should not be interpreted in an idealized or overly formal sense unless expressly so defined herein.

For the purposes of this application, the following terms will have the following meanings unless specifically stated otherwise:

The term "BMI" means body mass index, which is an individual's weight divided by their height squared ($kg/m^2$).

The term "fasted state" means the physiological state of an individual after a period of greater than about 6 hr. without food or calorie containing beverages. In this state, the individual's gastric emptying has been cleared and triglycerides are at a basal level.

The term "overweight" means the state of being significantly heavier than an optimal weight for a given individual. Definitions may vary widely, but for general purposes, a patient having a BMI of between about 25 and about 29.9 kg/m² will be considered to be overweight (Donato, PiSunyer et al. 1998). The invention is not affected by the exact definition of overweight as stated by the current BMI standard and all such definitions are to be considered as equivalents.

The term "obesity" means the state of being severely overweight or to have severe excessive weight. Definitions may vary widely, but for general purposes, a patient having a BMI≧30.0 kg/m² will be considered obese (Donato, PiSunyer et al. 1998). The invention is not affected by the exact definition of obesity as stated by the current BMI standard and all such definitions are to be considered as equivalents.

The term "fat load" means a dose of lipid sufficient to induce hyperlipidemia in a test subject and can take the form of an oral fat load, a fat-containing intravenous infusion, a high-fat foodstuff, a meal, a high fat beverage, or the like. It is also contemplated that a pharmaceutical agent may be developed and used to deliver the fat-load or a simulated fat-load.

The term "TRL V6" refers to TRL (triglyceride rich lipoprotein) particles or sub-fractions having a diameter between about 90 nm up to as much as about 170 nm, more typically having diameters between about 100-140 nm. The term "TRL V6" can also be defined with respect to the lipid methyl group NMR signal chemical shifts (ppm) corresponding to the estimated diameters as provided in Table I below.

The term "TRL V5" refers to large TRL particles having a diameter of between about 60 nm and about 80 nm (see Table 1 below for the associated NMR chemical shifts).

The term "chylomicron" refers to very large TRL particles having diameters that are larger than TRL V6. As such chylomicrons reters to TRL particles or sub-fractions having a diameter between from about 170 nm up to about 260 nm (see Table 1 below for their associated NMR chemical shifts). It is important to note that there is not a clear demarcation between TRL V5 and TRL V6 nor between TRL V6 and chylomicrons, such that there is a distribution of particle sizes for each subgroup that overlaps in the range between about 80-90 nm for TRL V5-6 and between about 140-170 nm for TRL V6 & chylomicrons.

The term "TRL V6 response" means the increase in TRL V6 triglyceride concentration and/or particle number in a patient or test mammal, typically in response to administration of a fat load or a high-fat diet. It is to be understood that under some circumstances, it may be advantageous to measure "V TRL", which for the purposes of this application is taken to mean a subgroup of very large TRL that contains both the TRL V6 and the TRL V5 particle subtypes, as a surrogate to measuring TRL V6 concentrations alone, in that under some circumstances, the TRL V5 concentration does not show a substantial response to fat loads, such that a response in "V TRL" may in particular circumstances track the TRL V6 response itself. This, however, does not hold true for measuring the total TRL or triglyceride concentration (or particle number) of the group as a whole (as for example total VLDL). It should be noted that the measure of the various TRL's may be reported as either concentration, ultimately meaning the concentration of triglycerides the designated TRL in the sample, or as the particle number, ultimately meaning the concentration of TRL particles in the sample. Both give the same results regarding the TRL V6 response or reduction therein.

The term "VLDL response" means the increase in particle size of TRL subclasses V1-6 as a group, in a patient or test mammal in response to administration of a fat load or high fat diet, which increase is the effect caused by the increase of TRL V6 concentration (or particle number) on the size distribution of VLDL particle sizes as a class (i.e. the change in the mean size of the TRL sub-populations, V1-V6).

A significant reduction in TRL V6 response means a statistically significant reduction in the measured TRL V6 concentration (or particle number or VLDL particle size). A reduction would be defined as a change in the TRL V6 response that falls below at least the $80^{th}$ percentile confidence interval of the lower bound of distribution of inter-occasion excursions measured in a population of patients in the absence of a test compound or weight loss pharmaceutical agent. For any given assay protocol, the actual confidence interval selected to determine a positive response to a test compound or weight loss pharmaceutical agent will depend on the desired predictive value of the assay protocol. As for example, an assay protocol desiring to provide fewer false positive reductions in TRL V6 response will select a higher percentile confidence interval, say for example, the $90^{th}$ percentile, or for example, the $95^{th}$ percentile. For assay protocols desiring fewer false negatives, lower confidence intervals would be suitable, as for example the $80^{th}$ percentile.

The term "weight loss pharmaceutical agent" means a pharmaceutical compound (which term includes peptides, antibodies, and the like), formulation, or composition, used or to be used for the treatment of obesity or overweight, in that the sought after therapeutic benefit is the inducement of weight loss in the patient and/or the maintenance of weight after a reduction of weight. It is understood that a weight loss pharmaceutical agent as used herein may comprise one or a combination of more than one active ingredients which may be taken as a single combined medicament or as a combination of medicaments. Similarly, the term "weight-loss" refers to actual weight loss and/or the maintenance of weight within a desired range, typically after a reduction in weight.

The term "biosample" includes whole blood, plasma, serum, urine, cerebral spinal fluid (CSF), lymph samples, stool samples, tissues, and/or body fluids in raw form and/or in preparations. However, whole blood or plasma biosamples may be particularly suitable for embodiments of the present invention. The biosamples can be from any target subject. Subjects', according to the present invention, can be any mammalian subjects (e.g., humans, canines, felines, bovines, caprines, ovines, equines, rodents (mice, rats, hamsters, guinea pigs or others), porcines, primates, monkeys, and/or lagomorphs). The animals can be laboratory animals or non-laboratory animals, whether naturally occurring, genetically engineered or modified, and/o whether being laboratory altered, lifestyle and/or diet altered or drug treated animal variations.

The term "automatic" means that substantially all or all of the operations so described can be carried out without requiring active manual input of a human operator, and typically means that the operation(s) can be programmatically directed and/or carried out.

The term "electronic" means that the system, operation or device can communicate using any suitable electronic media and typically employs programmatically controlling the communication between a control system that may be remote and one or more local NMR analyzers using a computer network.

Lipoproteins include a wide variety of particles found in plasma, serum, whole blood, and lymph, comprising various types and quantities of triglycerides, cholesterol, phospholipids, sphyngolipids, and proteins. These various particles permit the solublization of otherwise hydrophobic lipid molecules in blood and serve a variety of functions related to lipolysis, lipogenesis, and lipid transport between the gut, liver, muscle tissue and adipose tissue. In blood and/or plasma, lipoproteins have been classified in many ways, generally based on physical properties such as density or electrophoretic mobility. Classification based on nuclear magnetic resonance-determined particle size distinguishes at least 16 distinct triglyceride rich lipoprotein particle subtypes, including 5 subtypes of high density lipoproteins, 4 subtypes of low density lipoproteins, and 6 subtypes of very low density lipoproteins, designated TRL V1 through V6, and chylomicrons. Out of these lipoprotein subtypes, and in contrast to the other subtypes, the present invention has determined that the largest TRL particle subtype, TRL V6, can be used as a biomarker of triglyceride and/or lipoprotein metabolism in that concentrations of TRL V6, predictively become elevated following consumption of a fat-containing meal and then return to basal levels at some point subsequent to the meal as the test subject approaches a fasted state.

To correlate NMR characterizations of the TRL particles to estimated diameters, Table 1 below defines the chemical shift for the TRL V6 range as well as for TRL V5 and chylomicrons.

TABLE 1

Characteristics of Triglyceride Rich Lipoprotein
Subclasses Measured by NMR LipoProfile ® Analysis

| Subclass | TRL Subclass Components | NMR Chemical Shift (ppm) | Estimated Diameter (nm) |
|---|---|---|---|
| Chylomicrons | C-260 | 0.8477 | 260 |
| Chylomicrons | C-250 | 0.8470 | 250 |
| Chylomicrons | C-240 | 0.8464 | 240 |
| Chylomicrons | C-225 | 0.8457 | 225 |
| Chylomicrons | C-200 | 0.8443 | 200 |
| Chylomicrons | C-190 | 0.8440 | 190 |
| Chylomicrons | C-185 | 0.8436 | 185 |
| Chylomicrons | C-180 | 0.8429 | 180 |
| Chylomicrons | C-175 | 0.8422 | 175 |
| Chylomicrons | C-170 | 0.8416 | 170 |
| TRL V6 | V6-140 | 0.8402 | 140 |
| TRL V6 | V6-120 | 0.8388 | 120 |
| TRL V6 | V6-100 | 0.8374 | 100 |
| TRL V5 | V5-80 | 0.8361 | 80 |
| TRL V5 | V5-70 | 0.8347 | 70 |
| TRL V5 | V5-60 | 0.8333 | 60 |

Table 1 illustrates proton NMR chemical shifts of isolated triglyceride rich lipoprotein (TRL) subclasses (subfractions) that were measured relative to the internal reference signal of Ca EDTA (2.519 ppm). FIG. 1 illustrates NMR characteristic signals of exemplary TRL subclasses. NMR measurements were conducted on a 400 MHz spectrometer at 47 deg C. TRL subclasses identified as chylomicrons were isolated from postprandial plasma specimens obtained from human subjects after ingestion of a fat-containing meal. TRL subclasses identified as TRL V6 or TRL V5 were obtained from fasting plasma specimens obtained from hypertriglyceridemic human subjects. TRL subclasses were initially isolated by sequential ultracentrifugation (density<0.94 g/m for chylomicrons and <1.006 g/mL for TRL V5-V6) and further purified by gel filtration chromatography using 1% or 2% agarose beads (Bio-Rad, Hercules, Calif.) in a buffer containing 120 mM KCl, 5 mM EDTA, 1 mM $CaCl_2$, 50 mM $Na_2HPO_4$ and 0.2 g/L $NaN_3$, pH 7.4. Estimates of lipoprotein diameters were obtained from electron microscopy measurements on the isolated TRL subclasses.

Thus, while TRL V6 has been defined by diameter hereinabove, the NMR chemical shifts in Table 1 represent equivalents to the defined diameter ranges. Thus, using NMR evaluation, TRL V6 can also be defined as having chemical shifts between about 0.8374 to about 0.8402 and the neighboring TRL subfractions (e.g., TRL V5 and chylomicrons) have the chemical shifts also noted in Table 1. Accordingly, the definition of "TRL V6" also refers to any TRL subfraction that has the NMR chemical shifts noted above (+/–reasonable measurement ranges) when measured as described even if the actual test at issue employs a non-NMR evaluation methodology or defines the parameter with respect to density or in another manner rather than diameter.

For example, one known technique to measure very large TRL particles is flotation ultracentrifugation that employs a density-based separation. Redgrave et al. have characterized particles by their flotation rate ($S_f$, Svedberg units) with respect to their estimated diameters: $S_f$>400 includes particles>75 nm; $S_f$ 175-400 includes particles between 50-75 nm; $S_f$ 100-175 includes particles between 37-50 nm; and $S_f$ 20-100 includes particles between 20-37 nm. See, Redgrave et al., *Changes in plasma in very low density and low density lipoprotein content, composition, and size after a fatty meal in normo-and hypertriglyceridemic man*, Journal of Lipid Research, Vol. 20, pp. 217-229 (1979). See also, Karpe et al., *Differences in Postprandial Concentrations of Very-Low-Density Lipoprotein and Chylomicron Remnants Between Normotryglicyeridemic and Hypertriglyceridemic Men With and Without Coronary Heart Disease*, Metabolism, Vol. 48, No. 3 (March), 1999, pp. 301-307. Thus, even if not characterized based on size by the test method itself, if the density separated particles have about the chemical shifts noted above, the TRL particles are TRL V6 particles.

Furthermore, the present invention has determined that the post prandial triglyceride level correlates with elevation of TRL V6 concentration. These triglyceride levels can be attributed to either intra-lumenal triglyceride being hydrolyzed, fatty acids being absorbed from the gut and then re-esterified as triglyceride and transported into the lymphatics or the portal circulation as chylomicrons, or to VLDL secreted by the liver. In a state of positive energy balance, as for example, after excessive food intake, triglycerides are transported as a component of VLDL to adipose tissue for storage, as opposed to or in addition to other tissues, such as muscle, for use for energy through fatty acid oxidation. Thus a reduction in post prandial triglyceride levels would indicate an increase in fatty acid oxidation and/or a reduction in fat absorption and, in any case, correlates with a reduction in lipid storage. In some embodiments, the present invention demonstrates that specifically a reduction in TRL V6 concentration correlates with this reduction in lipid storage, such that determination of changes in the TRL V6 concentrations due to treatment with an investigational compound or with a weight loss pharmaceutical agent can be used as a biomarker for effects on triglyceride and/or lipoprotein metabolism, particularly as a marker for a reduction in lipid storage, including predicting whether a given individual patient will be a responder or non-responder to a given compound or weight loss pharmaceutical agent.

It will be understood that elevation of TRL V6 concentration (or particle number) may in some instances also be tracked by the increase in mean VLDL particle size, (mean or average size for all lipoprotein particles in the group of VLDL lipoprotein particles, TRL V1-V6) or even just large TRL=TRL V5+TRL V6). This is because the dominant component showing a changing concentration in response to a fat load in this group is the TRL V6 component as described above. Such a signal will be diluted by the signal from the other subtypes, but it may be possible to discern a VLDL response (change in ave. size) and thus a reduction in a VLDL response as a surrogate to measuring the TRL V6 response directly. It is noted that the overall concentration of VLDL V1-V5 as a group does not appreciably change and TRL V6 response is not generally detectable from measuring VLDL concentrations (as distinct from mean size) as a class.

Table 2 shows the statistical analysis of sibutramine induced reduction in area under the curve (AUC) from lipid load in comparison to placebo for large triglyceride rich lipoprotein subclasses measured by NMR. This data illustrates that Sibtramine reduced the TRL V6 response, but not the TRL V5 or chylomicrons response (note that only TRL V6 has a statistically significant change when measured as individual subgroups), thus indicating that TRL V6 is the biomarker. The data also demonstrates that in some circumstances the reduction in TRL V6 response can be detected even when the measurement includes signal from other subtypes, but not with all combinations of subsubtypes. In this particular study, TRL V6+chylomircons showed a significant change, but TRL V6+TRL V5 and TRL V6+TRL V5+chylomicrons did not produce a significant change. Note that where TRL V6 response can be equated with the response of a combination of subtypes, it is because the magnitude of the change in signal, which is due to the change of TRL V6 signal, is sufficiently large compared to the base line signal, to be a significant difference (i.e. the signal from TRL V6 in the base line signal dominates the combined signal so that a change in TRL V6 is reliably detected).

administering a fat load in a short time period, particularly after the individual patient has achieved a fasted state. Furthermore, these elevated concentrations return to basal levels as the human patient again approaches a fasted state. In addition, administration of certain weight loss pharmaceutical agents are now shown to reduce the magnitude of the TRL V6 response to a fat load.

Certain embodiments of the present invention are suitable for testing investigational weight loss pharmaceutical agents targeting one or more therapeutic targets, said targets each directly or indirectly modulating the triglyceride and/or lipoprotein metabolism pathway(s). Examples of therapeutic targets whose modulation can be assayed using the methods of the present invention are the $5\text{-HT}_{2C}$ receptor (agonists are being developed to treat obesity/overweight), the CB-1 receptor (antagonists), SNDRI (inhibitors), PDE-10 (inhibitors), and orexin-1 receptors (antagonists). Pharmaceuticals targeting $5\text{-HT}_{2C}$ receptors, CB-1 receptors, and/or inhibition of PDE-10, are particularly suited for the assay methods of the present invention. Other therapeutic targets may be readily found without undue experimentation by testing modulators of a target using the methods of the present invention and determining if a reduction in TRL V6 response is observed.

For studies in humans, including investigational studies on test therapeutic agents and for testing an individual's responsiveness/non-responsiveness to a given therapeutic agent, a

TABLE 2

Analysis of sibutramine induced reduction in AUC (5-11 hr. time points) from lipid load in comparison to placebo for large triglyceride rich lipoprotein subclasses measured by NMR and analyzed by the NMR LipoProfile ® III lipoprotein test (LipoScience, Inc., Raleigh, NC).

| Analyte(s) | Treatment | Geometric LS Mean | Sibutramine/Placebo Ratio | 90% C.I. | P-value |
|---|---|---|---|---|---|
| Chy | Sibutramine | 81.11 | 0.98 | (0.90, 1.07) | 0.721 |
|  | Placebo | 82.63 |  |  |  |
| TRL V5 | Sibutramine | 222.34 | 1.10 | (0.88, 1.38) | 0.474 |
|  | Placebo | 201.96 |  |  |  |
| TRL V6 | Sibutramine | 119.35 | 0.73 | (0.63, 0.84) | 0.001 |
|  | Placebo | 163.80 |  |  |  |
| TRL V6 + Chy | Sibutramine | 205.0 | 0.81 | (0.73, 0.91) | 0.004 |
|  | Placebo | 252.80 |  |  |  |
| TRL V6 + TRL V5 | Sibutramine | 364.08 | 0.88 | (0.77, 1.00) | 0.091 |
|  | Placebo | 414.39 |  |  |  |
| TRL V6 + V5 + Chy | Sibutramine | 458.04 | 0.89 | (0.80, 1.00) | 0.110 |
|  | Placebo | 512.27 |  |  |  |

P values < 0.05 are statistically significant;
P values > 0.05 are not statistically significant.

In rats, a significant reduction in TRL V6 concentration is readily measured due to typically high (that is readily measurable) basal levels. Thus studies on investigative compounds or weight loss pharmaceutical agents can be conducted in rats straightforwardly. In humans, however, basal levels are relatively low and tend to be closer to or below the limits of detection by current analytical methods, such as NMR spectroscopy on plasma samples.

In rat studies using diet induced obese rats fed on high fat diets, TRL V6 concentrations are constitutively elevated and reduction of TRL V6 concentration induced by administration of a pharmaceutical agent is indicative of the pharmaceutical agent's ability to modulate triglyceride and/or lipoprotein metabolism such that the storage of lipids in adipose tissue is reduced. In humans, the concentration of TRL V6 is ordinarily too low for reliable quantification. However, embodiments of the present invention have found that reliably measurable concentrations of TRL V6 can be induced by human patient is typically tested after waking and prior to consuming anything, as for example after fasting for about 5-10 hours, preferably between about 6 to 9 hours, as for example about 8 hours. Patients may drink water at any time before or during the testing period. The pretest period can be made to facilitate consistency as to meal content and timing prior to each testing session. A blood sample is then taken to provide a basal level measure of TRL V6 concentration or particle number for that patient when the patient is in a fasted state.

The patient can then administered a suitable fat load over the course of a relatively short time period, as for example, in about $\leq 40$ minutes, preferably in $\leq 20$ minutes. Depending on the study conducted or preferred routine testing conditions desired, one or more blood samples are then taken to determine the elevation in TRL V6 concentration in response to the fat load. Typically, one blood draw will be sufficient for routine testing using an established weight loss pharmaceutical agent, as for example to predetermine an individual patient's likely response to the agent in therapy. For other uses, it may be preferred to take multiple blood draws to obtain a complete TRL V6 response curve. The human TRL V6 response to a fat load, (i.e. elevation of TRL V6 concentration) typically begins about 2 hr. post fat load administration, peaking between about 4 hr. and about 6 hr. post fat load administration, and returning to basal concentrations between about 9 hr. and about 12 hr. post fat load administration. Note that there may be a shift in time course to later on-set/later return to basal levels when very high fat concentrations are administered. Such a shift typically sees an on set at about 4-6 hr., peaking at about 10 hr., and returning to basal levels between about 12-15 hr. A typical human TRL V6 response to a fat load is an elevation in plasma concentration from a basal level of about 0 mg/dL to about 35 mg/dl at a fasted state to between about 80 and about 250 mg/dL.

The human patient is then retested in conjunction with administration of the pharmaceutical agent. It is to be understood that the test in conjunction with the pharmaceutical agent may be conducted either before or after the test to determine the patient's normal TRL V6 response, provided that the pharmaceutical agent has cleared the patient's system prior to retesting, though this is not preferred. A typical reduction in human TRL V6 response indicative of a beneficial response to the test pharmaceutical agent or the weight loss pharmaceutical agent is a statistically significant reduction in the TRL V6 response. It is common to see the TRL V6 response be reduced by between about 20% to about 80%. Typical responses indicative of a favorable response may be about 50% reduction or more.

In one optimized embodiment, as for example, the routine use in predetermining a given patient's likelihood to respond favorably to a proposed therapy with a weight loss pharmaceutical agent, (i.e. to predict if the patient will be a responder or non-responder) a single administration of a fat load in conjunction with a dose of the proposed weight loss pharmaceutical agent may be suitable, such that the reduction in TRL V6 response may be determined from a predetermined patient population average TRL V6 response to the given fat load. In such an optimized embodiment, one blood draw prior to administration of the fat load and weight loss pharmaceutical agent and a single blood draw at a predetermined time point post fat load administration can be sufficient to determine if the weight loss pharmaceutical agent reduces the patient's TRL V6 response to the fat load, and thus pre-determine if the agent modulates that individual patient's triglyceride and/or lipoprotein metabolism. It may also be possible to determine a relevant TRL V6 response or reduction in TRL V6 response without an initial blood draw, but only taking a sample within a predetermined time range post fat load administration in conjunction with administration of the weight loss pharmaceutical agent. It is also contemplated that the administered fat load may be chemically and/or pharmaceutically induced or simulated fat load rather than a food-based fat load.

It will be understood that the specific clinical assay protocols used will depend upon the weight loss pharmaceutical agent being considered for therapy and that the determination of such protocols is within the ordinary skill in the art. As for example, the particular timing of administration of the agent and the second fat load will vary depending on the pharmacokinetics of the agent. One factor to consider is that the agent's blood levels be at an effective level prior to the administration of the fat load. Thus "in conjunction with" the pharmaceutical agent is understood to mean that the administration of the agent and the fat load are coordinated to allow the agent to be at an effective level in the patient so as to affect the distribution/metabolism of the fat load when it is administered. This can mean, depending on the specifics of the agent, that the agent is administered at the same time as the fat load or shortly thereafter, up to about 30 minutes post fat load administration, or that the agent is administered prior to the fat load by the period necessary to achieve an effective plasma level of the agent, say for example between about 0 and about 3 hours prior to administration of the fat load, as for example between 15 minutes and 30 minutes prior to administration of the fat load. If the pharmaceutical agent is administered as a prodrug or if active metabolites are important in the pharmacokinetics of the pharmaceutical agent, a longer time may be necessary to allow for appropriate plasma concentrations of the active moieties to accumulate. Determination of such dosing regimens are routine and well within the ordinary skill of the art.

Similarly, the timing and number of blood draws after administration of the fat load(s) may vary depending on the clearance rate of the agent, the important factor being that the agent's blood levels remain at an effective level until after the post fat load blood draw and should optimally be timed to correspond to the peak TRL V6 response based on the fat load administered.

Suitable fat loads comprise greater than about 30 g of fat, preferably greater than or equal to about 50 g of fat, preferably between about 60-70 g of fat. Fat loads comprising greater than or equal to about 80 g of fat may begin to induce longer times to TRL V6 response on set.

It will be understood that the exact composition of the fat load is unimportant and many suitable compositions may be readily formulated by the ordinarily skilled dietician. Suitable fat load formulations may be tailored to suit the desired study and/or according to patient population preferences. The important factor is that sufficient fat content and excessive over all caloric content be provided within a short time period to effect a measurable elevation in TRL V6 concentration in the absence of a test pharmaceutical agent.

The fat load may take any of a number of suitable forms as for example a prepared meal, a prepackaged meal, a single dose food stuff such as a snack bar, single dose liquid composition such as a prepackaged beverage or powdered beverage mix, or oral tablets or capsules. Examples of suitable compositions that would serve as fat loads are as follows:

Fat Load Example 1:

| Food Items | Portion | Energy (kcal) | Carb. (g) | Protein (g) | Fat (g) |
| --- | --- | --- | --- | --- | --- |
| Rice | 1 ice cream scoop (50 g) | 65 | 15 | 1 | 0 |
| Margarine (to be added into rice while it is hot) | 1 level dessertspoon (10 g) | 72 | 0.0 | 0.0 | 8.0 |
| Fried chicken wing (flour | 1 wing (70 g) | 223 | 6.7 | 19.1 | 13.3 |

-continued

| Food Items | Portion | Energy (kcal) | Carb. (g) | Protein (g) | Fat (g) |
|---|---|---|---|---|---|
| coated) | | | | | |
| Hash brown potatoes | 2 pieces (120 g) | 378 | 33.0 | 2.9 | 26 |
| Grade-A eggs (fried) | 1 egg (35 g) | 90 | 0.1 | 5.7 | 7.4 |
| Sliced cucumber | 5 slices (15 g) | 2 | 0.5 | 0 | 0 |
| Total | | 830 | 55 | 27 | 55 |
| Total Calories | | 830 | 229 | 108 | 495 |
| % Calories | | | 28% | 13% | 60% |

Fat Load Example 2:

| Menu | Protein (g) | Fat (g) | Carb. (g) | Total CAL. | % Protein | % Fat | % Carb. |
|---|---|---|---|---|---|---|---|
| 1 two-egg omelet | 12 | 14 | 2 | 180 | | | |
| 30 mL peanut butter | 7 | 16 | 7 | 200 | | | |
| 2 slices light bread, toasted | 4 | 0.5 | 17 | 80 | | | |
| 237 mL whole milk | 8 | 8 | 12 | 150 | | | |
| 2 strips bacon | 5 | 7 | 0 | 80 | | | |
| 30 mL margarine | 0 | 7 | 0 | 66 | | | |
| Meal totals (served) | 36 | 52.5 | 38 | 756 | 18.7% | 61.5% | 19.8% |

Fat load Example 3: Beverage: Volume of whole milk or cream or mixture thereof to provide desired amount of fat. For example about 150 mL to about 180 mL of whipping cream. A flavoring agent may be added to improve palatability.

Measurement of TRL V6 Concentration or Particle Number

TRL V6 response can be measured in any suitable manner. One currently known method of selectively measuring TRL V6 concentration or particle number is by NMR spectroscopy on plasma samples followed by deconvolution analysis to separate out the relative contributions of the various lipoprotein subtypes to the complete NMR signal. One such deconvolution method is the NMR LipoProfile®, NMR LipoProfile®-II and/or NMR LipoProfile® III, subclass particle analysis as provided by LipoScience, Inc., Raleigh, N.C. Likewise, mean VLDL particle size may be measured with the NMR LipoProfile® subclass particle analysis as well. See U.S. Pat. No. 5,343,389 to Otvos, U.S. Pat. No. 6,617,167, U.S. Pat. No. 4,933,844, and U.S. Pat. No. 7,243,030, for a description of this analytical technique. See also, US patent application 2005-0222504 for a description of NMR Clinical Analyzers. See also *Handbook of Lipoprotein Testing*, Chapter 31: "Measurement of lipoprotein subclass profiles by nuclear magnetic resonance spectroscopy", J. D. Otvos, AACC Press, Washington D.C., 2000, 2nd ed., pp 609-623, and Jeyarajah E J, Cromwell W C, Otvos J D. Lipoprotein particle analysis by nuclear magnetic resonance spectroscopy. *Clin Lab Med.* 2006; 26:847-70. The contents of these references are hereby incorporated by reference as if recited in full herein.

As a typical example, whole blood samples are collected into 2 ml EDTA blood collection tubes, inverted several times to mix well, and placed on ice. The samples are then centrifuged at approximately 3000 rpm for 10-15 minutes at 4° C. Upon completion of centrifugation, the tube is placed on ice and the plasma is drawn off. The plasma is place into a polypropylene tube and kept at 4° C. until analysis. Samples may be analyzed at any time up to about 4 days after collection. Samples are analyzed for TRL V6 response, as for example by NMR plasma lipoprotein analysis, as for example, the NMR LipoProfile®, the NMR LipoProfile®-II or the NMR LipoProfile®-III lipoprotein tests provided by LipoScience, Inc. of Raleigh, N.C.

NMR spectral data is analyzed as described in Jeyarajah et al., supra. Lipoprotein subclass concentrations are reported in lipid mass concentration units (TRL subclasses in units of mg/dL triglyceride) or, alternatively, in particle concentration units of nmol/L (nanomoles of particles per liter). The source information (NMR signal amplitude of each subclass) is transformed into these mass or particle concentration units by the analysis software, using a set of conversion factors obtained from chemical lipid and NMR analyses of isolated chylomicron, VLDL, LDL, and HDL subclass standards of normal lipid composition.

Figure 2:
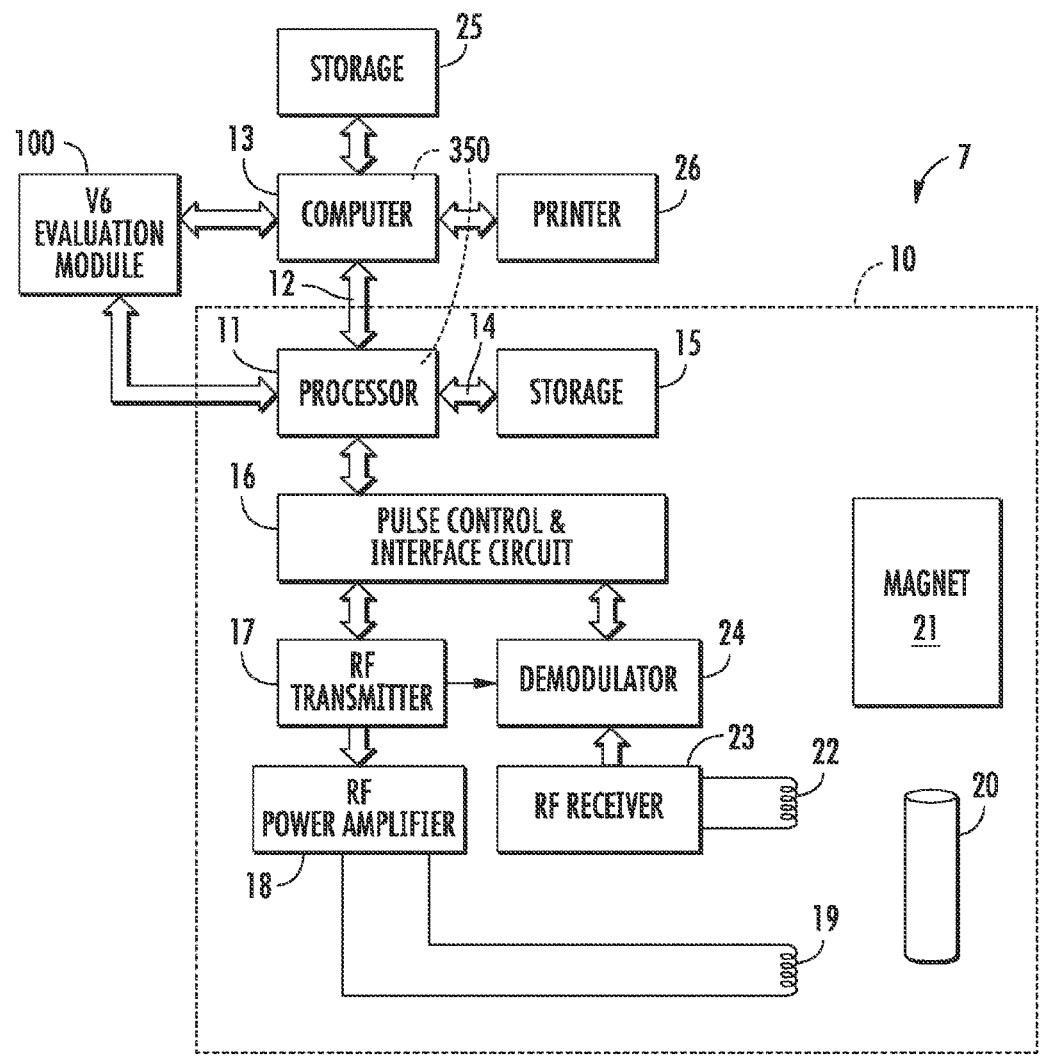
FIG. 2 is a schematic illustration of an NMR system according to embodiments of the present invention.

FIG. 2 illustrates an exemplary NMR analyzer system 7 that can be used to carry out the TRL V6 analysis and/or TRL V6 measurements using a TRL V6 evaluation module 100. The TRL V6 evaluation module 100 can be on-board the system in a signal processor and/or controller 11 or may reside partially or totally in a different local or remote processor such as on a server, client and/or other computer. Referring now to FIG. 2, the system 7 includes an NMR spectrometer 10 for taking NMR measurements of a biosample. In some embodiments, the spectrometer 10 is configured so that the NMR measurements are conducted at 400 MHz for proton signals; in other embodiments the measurements may be carried out at 360 MHz or another desired frequency. That is, other frequencies corresponding to a desired operational field strength may also be employed. Typically, a proton flow probe is installed, as is a temperature controller to maintain the sample temperature at 47+/−0.2 degrees C. Field homogeneity of the spectrometer 10 can be optimized by shimming on a sample of 99.8% $D_2O$ until the spectral linewidth of the HDO NMR signal is less than 0.6 Hz. The 90° RF excitation pulse width used for the $D_2O$ measurement is typically ca. 6-7 microseconds.

Referring again to FIG. 2, the spectrometer 10 is controlled by a digital signal processor and/or controller 11 or other signal processing unit. The processor/controller 11 should be capable of performing rapid Fourier transformations and may include for this purpose a hard-wired sine table and hardwired multiply and divide circuit. It may also include a data link 12 to an external or remote computer 13, and a direct-memory-access channel 14 which connects to an electronic storage unit 15.

The processor/controller 11 may also include a set of analog-to-digital converters, digital-to-analog converters and slow device I/O ports which connect through a pulse control and interface circuit 16 to the operating elements of the spectrometer. These elements include an RF transmitter 17 which produces an RF excitation pulse of the duration, frequency and magnitude directed by the digital computer 11, and an RF power amplifier 18 which amplifies the pulse and couples it to the RF transmit coil 19 that surrounds sample cell 20. The NMR signal produced by the excited sample in the presence of a 9.4 Tesla polarizing magnetic field produced by superconducting magnet 21 is received by a coil 22 and applied to an RF receiver 23. The amplified and filtered NMR signal is demodulated at 24 and the resulting quadrature signals are applied to the interface circuit 16 where they are digitized and input through the digital computer 11 to a file in the disc storage 15. The system 7 can include a deconvolving module located in the signal processor/controller 11 and/or totally or partially in another processor on a different computer, server or client that may be on-site or remote. See, US2005/0222504 for additional description of suitable clinical NMR analyzers, the contents of which are hereby incorporated by reference as if recited in full herein.

After the NMR data are acquired from the sample in the measurement cell 20, signal processing produces a data file which is a digital representation of the chemical shift spectrum which may be stored in electronic archival medical record storage 25. The computer 13, which may be personal, laptop, desktop, or other computer, processes the chemical shift spectrum and can provide a patient report, which is output to a printer 26 or electronically stored and relayed to a desired email address or URL. Those skilled in this art will recognize that other output devices, such as a display, may also be employed to provide the results.

It should be apparent to those skilled in the art that the functions performed by the computer 13 and its storage 25 may also be incorporated into the functions performed by the spectrometer's digital signal processor/controller 11 or in additional circuits in communication with the NMR spectrometer 10 and/or processor 11. Other interfaces and output devices may also be employed, as are well-known to those skilled in this art.

Figure 3:
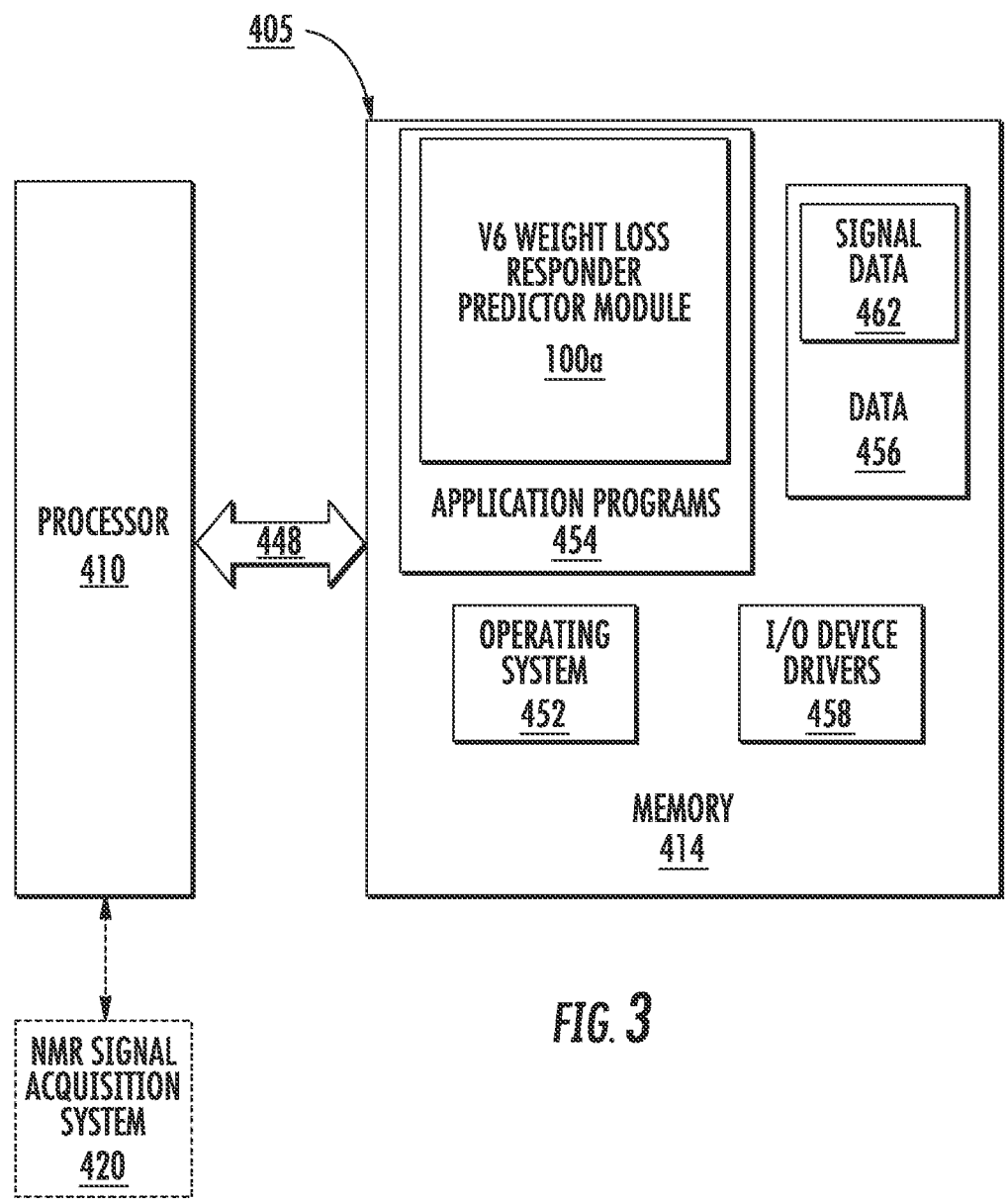
FIG. 3 is a schematic diagram of an exemplary data processing system according to embodiments of the present invention.
Figure 4:
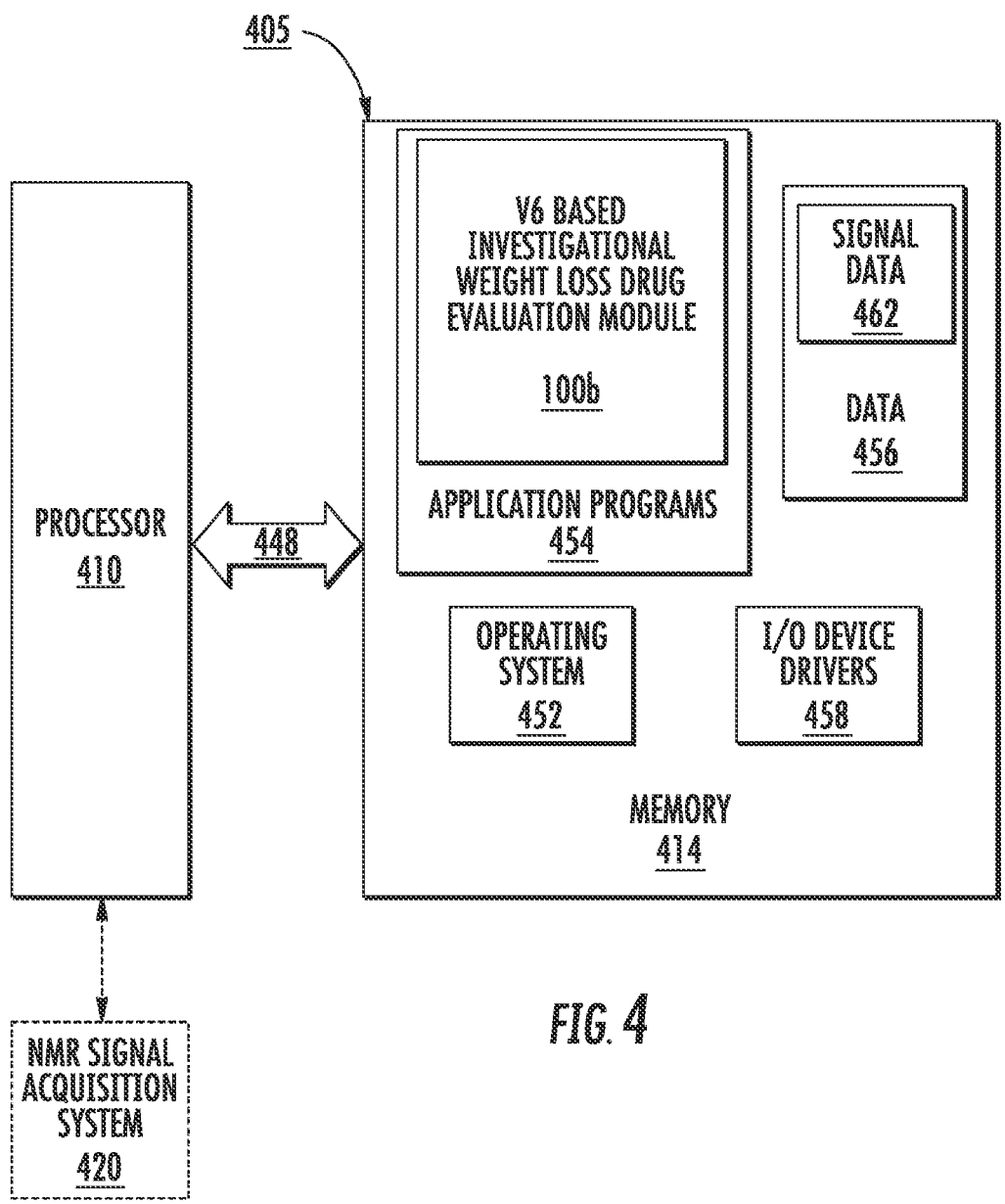
FIG. 4 is a schematic diagram of an exemplary data processing system according to embodiments of the present invention.

FIGS. 3 and 4 illustrate examples of TRL V6 evaluation modules 100a, 100b that can communicate with system 7, be on-board the system 7, and or analyze TRL V6 data measured by the system 7 or other measurement systems that can provide the TRL V6 data. As shown, FIGS. 3 and 4 illustrate exemplary embodiments of data processing systems that can be incorporated or provided as systems, methods, and/or computer program products in accordance with embodiments of the invention. The processor 410 (which can optionally be or communicate with processor 11 and/or computer 13 in FIG. 2) communicates with the memory 414 via an address/data bus 448. The processor 410 can be any commercially available or custom microprocessor.

The memory 414 is representative of the overall hierarchy of memory devices containing the software and data used to implement the functionality of the data processing system. 405. The memory 414 can include, but is not limited to, the following types of devices: cache, ROM, PROM, EPROM, EEPROM, flash memory, SRAM, and DRAM.

As shown in FIGS. 3 and 4, the memory 414 may include several categories of software and data used in the data processing system 405: the operating system 452; the application programs 454; the input/output (I/O) device drivers 458; the TRL V6 Weight Loss Responder Predictor Module 100a (FIG. 3) and/or the TRL V6 Based Investigational Weight Loss Drug Evaluation Module 100b (FIG. 4); and data 456.

The data 456 may include TRL NMR subclass signal (constituent and/or composite spectrum lineshape) data 462 which may be obtained from a data or signal acquisition system 420 (such as system 7 shown in FIG. 2). For each patient or animal model biosample, the data can include TRL V6 specific data values, or TRL V6 with other subfraction data (e.g., chylos and/or TRL V5). As will be appreciated by those of skill in the art, the operating system 452 may be any operating system suitable for use with a data processing system, such as OS/2, AIX or OS/390 from International Business Machines Corporation in Armonk, N.Y., Windows CE, Windows NT, Windows 95, Windows 98, Windows 2000, or Windows XP from Microsoft Corporation, Redmond, Wash., Palm OS from PalmSource, Inc., Sunnyvale, Calif., Mac OS from Apple Computer, Inc, UNIX, FreeBSD, or Linux, proprietary operating systems or dedicated operating systems, for example, for embedded data processing systems.

The I/O device drivers 458 typically include software routines accessed through the operation system 452 by the application programs 454 to communicate with devices such as I/O data port(s), data storage 456 and certain memory 414 components and/or the data acquisition system 420. The application programs 454 are illustrative of the programs that implement the various features of the data processing system 405 and preferably include at least one application that supports operations according to embodiments of the present invention. Finally, the data 454 represents the static and dynamic data used by the application programs 454, the operating system 452, the I/O device drivers 458, and other software programs that may reside in the memory 414.

While embodiments of the present invention are illustrative, for example, with reference to the Modules 100a, 100b being an application program in FIGS. 3 and 4, as will be appreciated by those of skill in the art, other configurations may also be utilized while still benefiting from the teachings of embodiments of the present invention. For example, the Modules 100a, 100b may also be incorporated into the operating system 452, the I/O device drivers 458, or other such logical division of the data processing system 405. Thus, embodiments of the present invention should not be construed as limited to the configurations of FIGS. 3/4, which are intended to encompass any configuration capable of carrying out the operations described herein. In certain embodiments, the Module 100a and/or 100b may include computer program code for communicating with a remote control system (local or offsite).

It will be appreciated that the methods, systems and computer program products of the present invention are not limited by the means of measuring the TRL V6 response or VLDL response in that new methods of making such subtype-distinct measurements will likely be discovered in the future or in that conventional methods may be modified to allow for such measurement. As for example, it may become possible to measure TRL V6 response by immunoassay techniques if and when TRL V6 specific antigens become known and specific antibodies are developed to such antigens. It may also become possible to distinguish and quantify TRL V6 specific proteins or other TRL V6 specific components and thus new methods to measure the TRL V6 response may become possible or ultracentrifugation and flotation evaluation or other conventional methods may be modified to provide suitable TRL V6 information. Such methods will be understood by those of ordinary skill in the art to be equivalent to methods using NMR techniques herein described.

Figure 5:
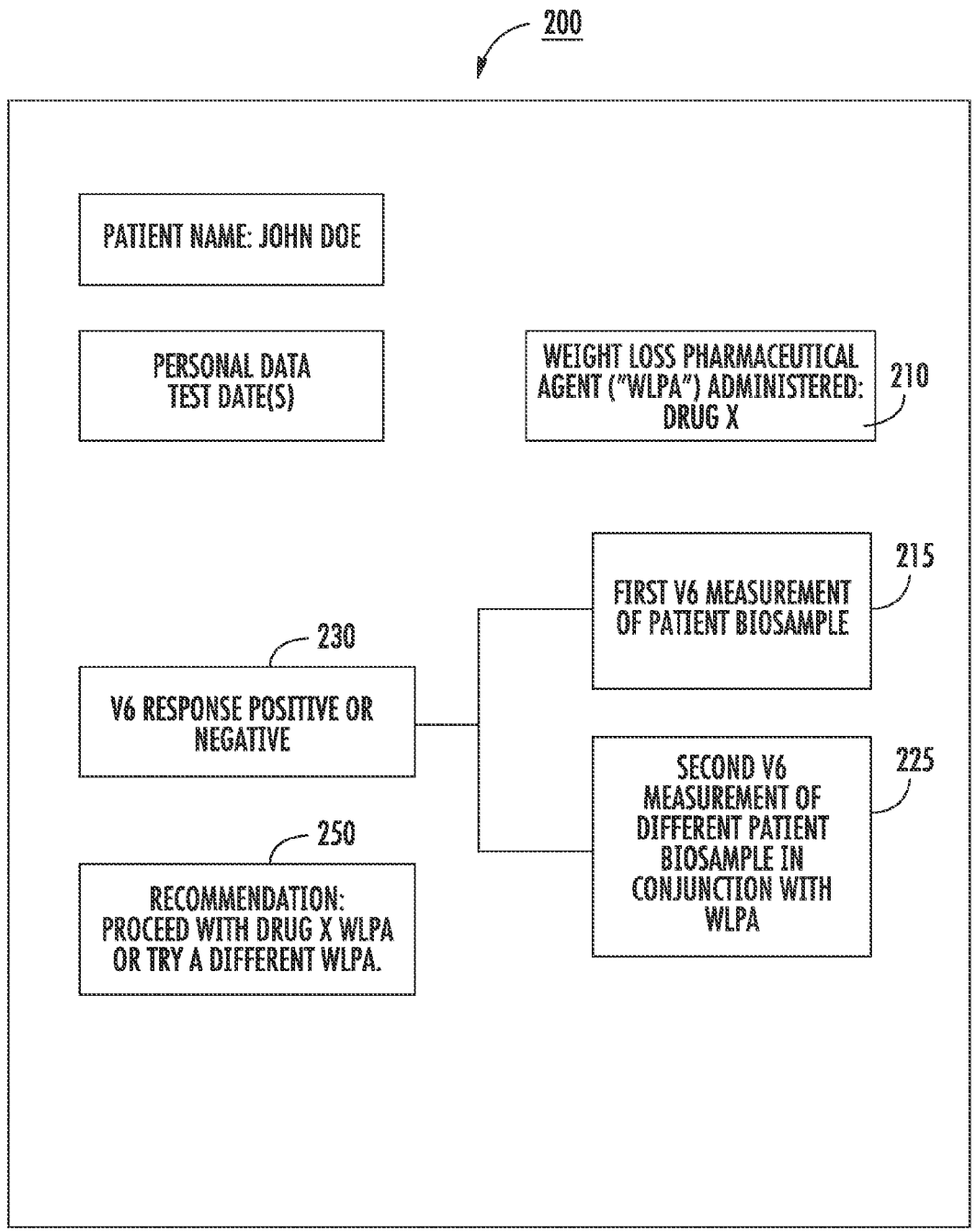
FIG. 5 is a schematic of an exemplary patient test report of a TRL V6 evaluation according to embodiments of the present invention.

FIG. 5 illustrates an exemplary patient report 200. As shown, the report 200 can include the patient's name 201 and personal data 205 (such as specimen collection dates, weight, fat load administration and drug administration times). The report 200 can also include the name of the weight loss pharmaceutical agent (WLPA) administered in conjunction with the collection of the second biosample from the patient (block 210). The report 200 can optionally provide two different TRL V6 measurements or evaluations, one of a sample that is indicative of a patient's normal TRL V6 response and another that is taken in conjunction with the WLPA (blocks 215, 225). The report 200 can indicate whether there was a positive TRL V6 response associated with the WLPA (block 230). The report 200 can include a recommendation that the patient proceed with the WLPA or that the WLPA is not likely to be beneficial for this patient (block 250). The recommendation can indicate the percent reduction in TRL V6 (not shown) if any and may provide relevant statistics for those that are likely to respond the reduction is at least 80%. This may allow a clinician to proceed with the WLPA if the patient is a borderline responder (e.g., 60-75% reduction).

Embodiments of the present invention are explained in greater detail in the following non-limiting Examples.

EXAMPLE 1

Cross Therapeutic Target Rat Study

The ability of investigational weight loss pharmaceutical agents to reduce the TRL V6 concentration in rats is shown with three compounds targeting different mechanisms of action including a known potent and selective $5\text{-HT}_{2C}$ receptor agonist, a known potent and selective CB-1 receptor antagonist/inverse agonist, and a potent SNDRI (sibutramine). Each of these compounds are known to induce weight loss in rats and thus the biomarker of reduction in TRL V6 concentration correlates to the investigational weight loss pharmaceutical agents' ability to induce weight loss. Conversely, an opiate antagonist, (naltrexone) which is known to be ineffective in inducing weight loss in rats or in overweight and obese human subjects (Malcolm R et al., Int. J. Obes. 1985; 9(5):347-53), is shown to not reduce the TRL V6 concentration in rats, again correlating the biomarker of reduction in TRL V6 concentration to the investigational weight loss pharmaceutical agents' ability to induce weight loss.

DIO-LE rats maintained on a high fat chow are administered either a vehicle dose or an acute dose of test compound. At specified time points post dose, animals are sacrificed and blood is collected in blood sample tubes containing EDTA and processed essentially as described above. Samples are analyzed by NMR LipoProfile® lipoprotein sub-particle test with report of all particle subtypes (specifically the TRL V6 concentration or particle number).

The 10 mg/kg dose of the $5\text{-HT}_{2C}$ agonist reduces circulating concentration of TRL V6 by about 90% at 2 hr. post dose and about 80% at about 8 hr. post dose. TRL V6 plasma concentration and VLDL mean particle size return to baseline concentrations by about 18 hr. post dose.

The 0.3 mg/kg dose of the CB-1 antagonist reduces circulating concentration of TRL V6 and VLDL particle size by about 75% at about 1 hr. post dose and about 3 hr. post dose. The response reductions continue at about 50% at about 5 hr. post dose. TRL V6 plasma concentration return to baseline concentration by about 18 hr. post dose.

The 3 mg/kg dose of the SNDRI reduces circulating concentration of TRL V6 and VLDL mean particle size by about 78% at 2 hr. post dose and 5 hr. post dose. TRL V6 plasma concentration return to baseline concentration by about 18 hr. post dose.

In comparison, a 10 mg/kg orally administrated dose of naltrexone had a minimal effect on circulating TRL V6 levels. Naltrexone reduced TRL V6 levels only 30% 2 hr. post dose. The TRL V6 level returned to baseline levels at 5 hrs and were unchanged at 18 hr. post dose.

| | | | Reduction in TRL V6 Response | | |
|---|---|---|---|---|---|
| Target | Compound | Dose | T1-(ie 2 hrs) | T2-(ie 5 hrs) | T3-(ie 18 hrs) |
| 5HT2c Angonist | LY2140119 | 10 mg/kg | 90% | 84% | 0% |
| CB-1 Antagonist | LY2509419 | 0.3 mg/kg | 75% | 50% | 0% |
| SNDRI | Sibutramine | 3 mg/kg | 78% | 78% | 0% |
| OpRA Antagonist | Naltrexone | 10 mg/kg | 30% | 0% | 0% |

EXAMPLE 2

Human Study with a SNDRI (Sibutramine)

A SNDRI (sibutramine) known to be able to induce weight loss in humans is tested to correlate its ability to reduce TRL V6 response plasma concentrations and V-TRL response in humans in an exploratory biomarker study employing a single-blind, crossover design, comparing sibutramine and placebo in hypertriglyceridemic and overweight and obese but otherwise healthy subjects.

Three cohorts containing 6 subjects each, undergo three periods during the study. Subjects are fasted overnight and two fasting blood draws are obtained, followed by breakfast at approximately 07:00 hours. Placebo or sibutramine is administered at approximately 10:00 hours. Blood sampling is begun approximately 1 hr. after the start of breakfast and continues at hourly intervals for 7 hr., and then every 2 hr. for the next 10 hr. A lunch according to Example fat load 2 is served at approximately 12:00 hours (approximately 60 to 65 g of fat). No other food is permitted until 12 hr. post fat load administration. Subjects are released after the last blood sampling for a 4 to 8-day washout period before return for the second testing period of the study. After the washout period, subjects are again fasted overnight. The procedures are then repeated as in the first testing period of the study except that each subject crosses over to receive the alternate treatment, sibutramine or placebo. Blood samples are collected, processed and analyzed essentially as described in Example 1 above.

TRL V6 responses and V-TRL responses are observed during the period from 5 to 11 hr. post fat load. The AUC (area under the response curve) from 5-11 hr. post fat load administration is calculated and statistically analyzed using a mixed effects model analysis to compare the sibutramine arms with the placebo arms. The sibutramine treated arms on average show a statistically significant decrease in the TRL V6 response of about 28%, but does not show a significant change in the plasma concentrations of any of the TRL V1, V2, V3, V4, or V5 subtypes. A statistically significant decrease in mean V-TRL response is also observed, although the magnitude of this change is found to be smaller than the change in TRL V6 response. In most subjects, the administration of sibutramine reduced the magnitude of the TRL V6 response and V-TRL response compared to their placebo-treated responses. Thus the reduction of the TRL V6 response and V-TRL response induced by the SNDRI correlates with the SNDRI known ability to induce weight loss in humans.

EXAMPLE 3

Human Study with a 5-HT$_{2C}$ Receptor Agonist

A potent and selective 5-HT$_{2C}$ receptor agonist known to induce weight loss in rats and monkeys and believed to induce weight loss in humans is tested to correlate its ability to reduce TRL V6 response in a single-center, inpatient/outpatient, double-blind (blinded as to subject and investigator), randomized, placebo-controlled, single-dose, dose-escalation study in overweight or obese but otherwise healthy subjects.

Subjects in each cohort participate in four dosing periods (three periods with active drug and one period with placebo, following a randomization code to ensure that no subject receives placebo twice). Subjects are fasted overnight and a pre-dose blood collection is obtained. Subjects are then given an oral dose of compound or placebo. At 2 hr. post dose, an oral fat load according to fat load Example 2, above, is administered to the subjects. Blood samples are collected and processed at regular intervals over the 0 to 12 hr. post-dose time period and analyzed essentially as in Example 2 above. The AUC for TRL V6 response is estimated over the 0 to 12 hr. post-dose sampling period to evaluate the TRL V6 response to an oral fat load in the presence of compound or placebo.

Using a mixed effects model to statistically compare the TRL V6 response for compound treated arms and placebo treated arm, a statistically significant reduction in the TRL V6 response for the compound arms is seen compared to the placebo-related response to the high-fat meal. The relationship between TRL V6 response and compound plasma exposure is nonlinear, with a steep reduction in the magnitude of TRL V6 response at the higher plasma drug concentrations. Thus the reduction of the TRL V6 response and VLDL response induced by the 5-HT$_{2C}$ agonist correlates with the compound's known ability to induce weight loss in rats.

The foregoing is illustrative of the present invention and is not to be construed as limited to the specific embodiments disclosed. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and also structural equivalents thereof, which includes equivalent structures thereof.

I claim:

1. A system for assessing a patient's likelihood of responding favorable to a weight-loss pharmaceutical agent, comprising:

an NMR spectrometer configured to measure triglyceride rich lipoprotein (TRL) V6; and at least one processor in communication with the NMR spectrometer, wherein the at least one processor is configured to predict whether a patient is likely to respond favorably to the weight loss pharmaceutical agent based on at least one NMR derived TRL V6 measurement on at least one patient biosample taken after the patient has been administered a fat load in conjunction with administration of the weight loss pharmaceutical agent, wherein the at least one processor is configured to compare said TRL V6 measurement with either a standard TRL V6 measurement in response to the fat load in the absence of the weight loss pharmaceutical agent, or with a second NMR derived TRL V6 measurement on at least one patient biosample taken after the patient has been administered a fat load in the absence of the weight loss pharmaceutical agent, and determine whether there is a significant reduction in TRL V6 for the sample taken in conjunction with the weight loss pharmaceutical agent, wherein a significant reduction in TRL V6 indicates a patient is likely to respond favorably to the weight loss pharmaceutical agent.

* * * * *

UNITED STATES PATENT AND TRADEMARK OFFICE
CERTIFICATE OF CORRECTION

PATENT NO. : 8,355,877 B2
APPLICATION NO. : 12/743034
DATED : January 15, 2013
INVENTOR(S) : Jennifer K. Leohr It is certified that error appears in the above-identified patent and that said Letters Patent is hereby corrected as shown below:

Title Page, Other Publications, Column 2, Line 3, Delete "Mem" and insert -- Men --, therefor.

Column 1, Line 6-7, Delete "This application........Dec. 19, 2007." and insert -- This application is a United States national phase entry, pursuant to 35 U.S.C.371, of PCT/US2008/087386, filed December 18, 2008 which claims the benefit of United States provisional patent application serial number 61/014881, filed December 19, 2007. --, therefor.

Signed and Sealed this
Twenty-sixth Day of February, 2013

Teresa Stanek Rea
*Acting Director of the United States Patent and Trademark Office*